US008482735B2

(12) United States Patent
Okada

(10) Patent No.: US 8,482,735 B2
(45) Date of Patent: Jul. 9, 2013

(54) LASER GAS ANALYZER

(75) Inventor: Masanori Okada, Musashino (JP)

(73) Assignee: Yokogawa Electric Corporation, Musashino-Shi, Tokyo (JP)

( * ) Notice: Subject to any disclaimer, the term of this patent is extended or adjusted under 35 U.S.C. 154(b) by 0 days.

(21) Appl. No.: 13/400,924

(22) Filed: Feb. 21, 2012

(65) Prior Publication Data

US 2012/0212744 A1  Aug. 23, 2012

(30) Foreign Application Priority Data

Feb. 21, 2011  (JP) ................................. 2011-034826

(51) Int. Cl.
*G01N 21/61* (2006.01)

(52) U.S. Cl.
USPC .......................................... 356/437; 356/438

(58) Field of Classification Search
USPC ............... 356/432–437, 39–42; 250/343, 349
See application file for complete search history.

(56) References Cited

U.S. PATENT DOCUMENTS

| | | | | |
|---|---|---|---|---|
| 3,792,272 | A * | 2/1974 | Harte et al. ................... | 250/343 |
| 4,686,683 | A * | 8/1987 | Martin ............................ | 372/94 |
| 4,914,720 | A * | 4/1990 | Knodle et al. ................. | 250/343 |
| 5,173,749 | A * | 12/1992 | Tell et al. ....................... | 356/437 |
| 5,179,580 | A * | 1/1993 | Komatani et al. .............. | 378/44 |
| 5,489,981 | A * | 2/1996 | Killpatrick et al. ........... | 356/459 |
| 5,525,788 | A * | 6/1996 | Bridgelall et al. ........ | 235/462.08 |
| 5,800,348 | A * | 9/1998 | Kaestle .......................... | 600/322 |
| 5,867,514 | A * | 2/1999 | Anderson .................. | 372/38.01 |
| 6,313,464 | B1 * | 11/2001 | Schrader ....................... | 250/349 |
| 6,650,443 | B1 * | 11/2003 | Izumi ............................ | 358/475 |
| 7,697,580 | B2 * | 4/2010 | Smith et al. ............... | 372/29.021 |
| 2007/0013899 | A1 * | 1/2007 | Wolters et al. ............. | 356/237.2 |
| 2009/0227887 | A1 * | 9/2009 | Howard et al. ............... | 600/531 |

FOREIGN PATENT DOCUMENTS

| | | |
|---|---|---|
| JP | 59-027245 A | 2/1984 |
| JP | 02-126178 A | 5/1990 |
| JP | 03-067115 A | 3/1991 |
| JP | 11-148898 A | 6/1999 |
| JP | 2011-013126 A | 1/2011 |

OTHER PUBLICATIONS

Tamura, Kazuto et al., "TDLS200 Tunable Diode Laser Gas Analyzer and its Application to Industrial Processes", Yokogawa Technical Report, 2010, pp. 51-54, vol. 53 (2).
Japanese Office Action mailed Feb. 21, 2013, issued in corresponding Japanese Patent Application No. 2011-034826.

* cited by examiner

*Primary Examiner* — Sang Nguyen
(74) *Attorney, Agent, or Firm* — Westerman, Hattori, Daniels & Adrian, LLP

(57) ABSTRACT

A laser gas analyzer which can include a light source unit including a diode laser that irradiates a gas to be measured with laser light while scanning a wavelength thereof; a detection unit including a light receiving element, a gain-variable amplifier into which an output signal of the light receiving element is input, an A/D converter into which the output signal of the amplifier is input, and an arithmetic processing unit that performs a concentration analysis of the gas to be measured; a peak-to-peak detector that detects a peak-to-peak value of the output data of the A/D converter in each scan of the wavelength of the laser light irradiated from the diode laser; and a gain adjustment unit that, when the output signal of the peak-to-peak detector deviates from a preset threshold, adjusts the gain of the amplifier in a direction of bringing the output signal back to within the threshold.

4 Claims, 2 Drawing Sheets

LASER GAS ANALYZER

BACKGROUND

1. Technical Field

The present disclosure relates to a laser gas analyzer. In particular, the present disclosure relates to dynamic auto gain control of a received optical signal.

2. Related Art

A laser gas analyzer using the tunable diode laser absorption spectroscopy (TDLAS) method has the following advantages. That is, the analyzer can measure the concentration of a high-temperature component to be measured or a component to be measured containing a corrosive gas or the like only by irradiating the component to be measured with light from a tunable diode laser with high component selectivity, in a non-contact manner, at high speed, and in real time without being subject to interference of other components.

FIG. 2 is a block diagram exemplifying a laser gas analyzer in the related art using the TDLAS method. The analyzer includes a light source unit and a detection unit. The light source unit contains a diode laser. The diode laser irradiates an atmosphere of a gas to be measured with measuring laser light. The detection unit contains a light receiving element and an arithmetic processing unit. The light receiving element detects the measuring laser light that has passed through the measuring space of the atmosphere of the gas to be measured. The arithmetic processing unit processes an output signal of the light receiving element.

The laser gas analyzer shown in FIG. 2 measures an inherent light absorption spectrum of molecules, which are components to be measured present ranging from an infrared region to a near infrared region, by using a diode laser in which the emission wavelength spectral line width is extremely narrow. The molecule-inherent light absorption spectrum corresponds to a molecule vibration or a rotation energy transition. Inherent absorption spectra of many molecules including $O_2$, $NH_3$, $H_2O$, CO, and $CO_2$ are in the infrared to near infrared regions. The concentration of the target component can be calculated by measuring the absorbed amount (absorbance) of light at a specific wavelength.

As shown in FIG. 2, a diode laser 11 is provided in a light source unit 10. The diode laser 11 irradiates an atmosphere of a gas to be measured 20 with measuring laser light. The line width of the emission wavelength spectrum of the laser light irradiated by the diode laser 11 is extremely narrow. The emission wavelength can be changed only by changing the laser temperature or the drive current. Thus, any one absorption peak in the absorption spectrum can be measured.

Therefore, the absorption peak can be selected by the laser gas analyzer without being affected by an interfering gas. Moreover, the analyzer has high wavelength selectivity and is not affected by other interfering components. Therefore, the analyzer can directly measure a process gas without removing the interfering gas in a stage prior to measurement.

The exact spectrum that does not overlap with interfering components can be measured by scanning the emission wavelength of the diode laser 11 near one absorption line of the component to be measured. The shape of the spectrum changes due to the broadening phenomenon of the spectrum caused by variations (environmental variations) of the temperature of the gas to be measured, the pressure of the gas to be measured, and coexisting gas components. Such environmental variations are involved in actual process measurement and thus compensation is necessary.

Thus, the analyzer in FIG. 2 uses the spectral area method. According to the spectral area method, the absorption spectrum is measured while the emission wavelength of the diode laser 11 is scanned. The spectral area is thereby determined. The component concentration is calculated based on the spectral area.

Other laser gas analyzers use the peak height method, 2f method or the like. According to the peak height method, the concentration of a component to be measured is determined from the peak height of an absorption spectrum. According to the 2f method, a wavelength signal for scanning is modulated to obtain a modulated waveform having a frequency twice the frequency of the wavelength signal. Then, the concentration of a component to be measured is determined based on a P-P (peak to peak) value of the modulated waveform. These methods are likely to be affected by variations of the temperature, pressure, or coexisting gas components.

In contrast, the spectral area method is not in principle affected by differences of coexisting gas components (the spectral area is almost the same regardless of coexisting gas components). Even if the pressure is varied, the spectral area in principle changes linearly.

According to the peak height method and 2f method, all three variable factors (the temperature, pressure, or coexisting gas components) nonlinearly affect measured values. If these variable factors coexist, it is difficult to make compensation. According to the spectral area method, on the other hand, linear compensation can be made for gas pressure variations and nonlinear compensation can be made for gas temperature variations. Therefore, accurate compensation can be realized.

The measuring laser light having passed through the atmosphere of the gas to be measured 20 is received by a light receiving element 31 provided in a detection unit 30. The light receiving element 31 converts the received laser light into an electric signal.

An output signal from the light receiving element 31 is adjusted by a gain-variable amplifier 32 so that the signal has an appropriate amplitude level. Subsequently, the output signal is input into an A/D converter 33. The A/D converter 33 converts the signal into a digital signal.

Output data from the A/D converter 33 is added up by an integrating meter 34 before being stored in a memory 35. The additions and storages are repeated in synchronization with scans of the wavelength of the diode laser 11 a predetermined number of times (for example, a few hundred to a few thousand times). Accordingly, noise contained in a measurement signal (output data) is removed. As a result, the output data is smoothed. The smoothed output data is input into a CPU 36.

The CPU 36 performs arithmetic processing such as the concentration analysis of the gas to be measured based on the measurement signal from which noise has been removed. Further, the CPU 36 adjusts the gain of the amplifier 32 if the amplitude level of the output signal of the light receiving element 31 is not appropriate as the level of a signal input into the A/D converter 33.

In the literature "Laser Gas Analyzer TDLS200 and Its Application to Industrial Processes by Kazuto Tamura and three others, Yokogawa Technical Report, Yokogawa Electric Corporation, 2010, Vol. 53, No. 2 (2010), pp. 51-54", the principle of measurement, features, and concrete measurement examples of the laser gas analyzer in which tunable diode laser absorption spectroscopy is applied are described. This document is incorporated herein in its entirety.

SUMMARY

A laser gas analyzer includes: a light source unit including a diode laser that irradiates a gas to be measured with laser light while scanning a wavelength thereof; a detection unit including a light receiving element that detects the laser light having passed through the gas to be measured, a gain-variable amplifier into which an output signal of the light receiving element is input, an A/D converter into which the output signal of the amplifier is input, and an arithmetic processing unit that performs a concentration analysis of the gas to be measured based on output data of the A/D converter; a peak-to-peak detector that detects a peak-to-peak value of the output data of the A/D converter in each scan of the wavelength of the laser light irradiated from the diode laser; and a gain adjustment unit that, when the output signal of the peak-to-peak detector deviates from a preset threshold, adjusts the gain of the amplifier in a direction of bringing the output signal back to within the threshold.

BRIEF DESCRIPTION OF DRAWINGS

The advantages of the invention will become apparent in the following description taken in conjunction with the drawings, wherein.

DETAILED DESCRIPTION

Figure 1:
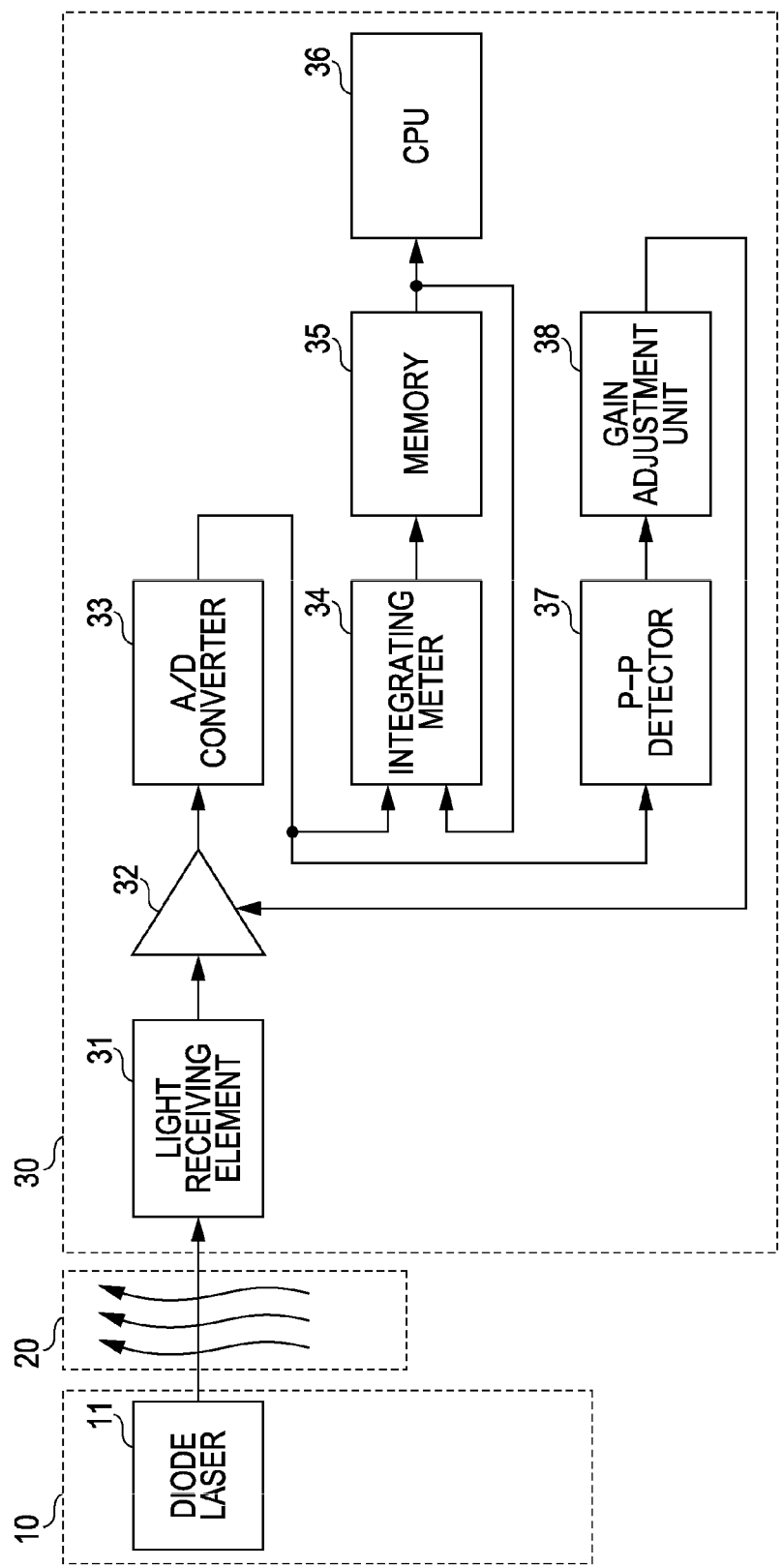
FIG. 1 is a block diagram showing a laser gas analyzer according to an embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
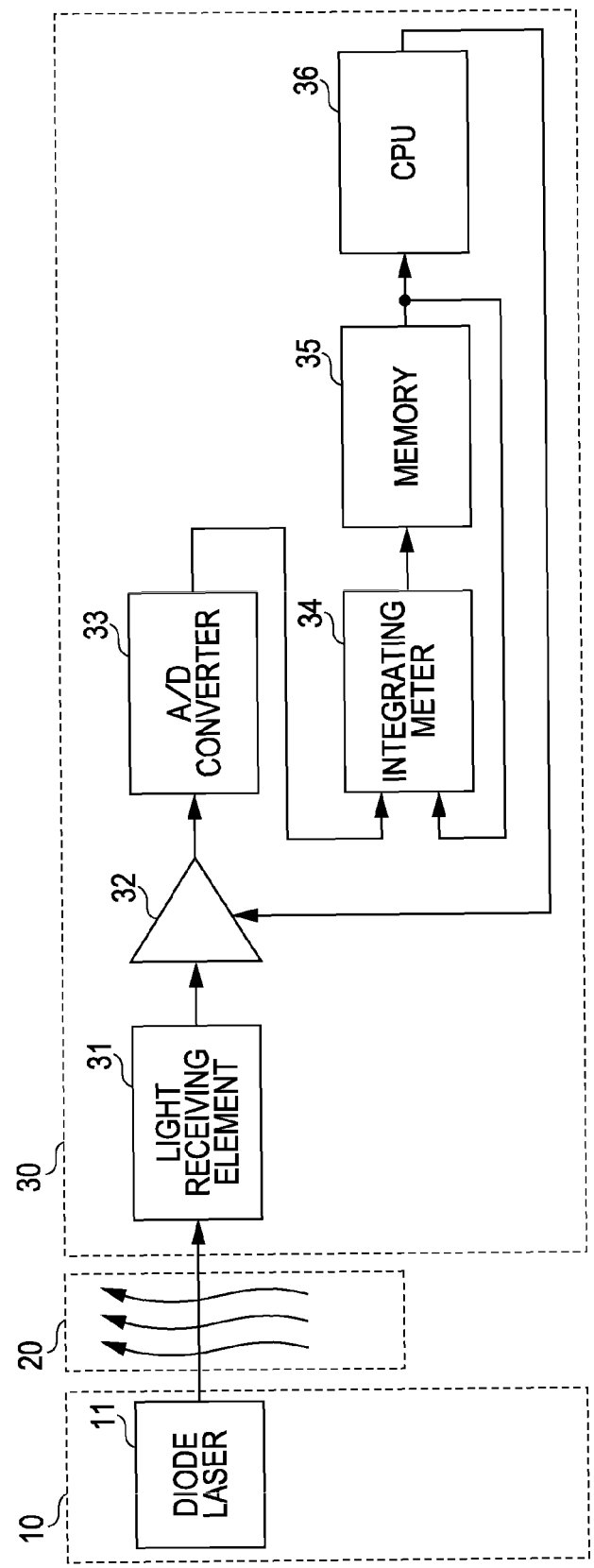
FIG. 2 is a block diagram exemplifying a laser gas analyzer in the related art.

Incidentally, in a laser gas analyzer as shown in FIG. 2, data is smoothed by, as described above, removing noise contained in a measurement signal. Thus, output data from the A/D converter 33 is added up by the integrating meter 34 before being stored in the memory 35. The additions and storages are repeated in synchronization with scans of the wavelength of the diode laser 11 a few hundred to a few thousand times. In a period of a sequence of analysis processing including a wavelength scan, an addition, and a storage that is repeated a few hundred to a few thousand times, it is preferable to maintain the level of signals input into the A/D converter 33 constant by adjusting the gain of the amplifier 32.

However, if an abrupt environment change occurs such as extraneous noise arising suddenly in the period of a sequence of analysis processing, it becomes more difficult for the CPU 36 to cope with environment changes by adjusting the gain of the amplifier 32 based on software processing. Thus, for example, measured data is clipped. As a result, there is posed a problem in that analysis results in the period of analysis processing become data containing error.

An object of the present disclosure is to realize a laser gas analyzer capable of appropriately adjusting the gain of an amplifier in each scan of the wavelength of laser light (for each sampling).

A laser gas analyzer according to a first aspect of the present disclosure includes: a light source unit including a diode laser that irradiates a gas to be measured with laser light while scanning a wavelength thereof; a detection unit including a light receiving element that detects the laser light having passed through the gas to be measured, a gain-variable amplifier into which an output signal of the light receiving element is input, an A/D converter into which the output signal of the amplifier is input, and an arithmetic processing unit that operates a concentration of the gas to be measured based on output data of the A/D converter; a peak-to-peak detector that detects a peak-to-peak value of the output data of the A/D converter in each scan of the wavelength of the laser light irradiated from the diode laser changes; and a gain adjustment unit that, when the output signal of the peak-to-peak detector deviates from a preset threshold, adjusts the gain of the amplifier in a direction of bringing the output signal back to within the threshold.

A second aspect is the laser gas analyzer according to the first aspect, wherein the threshold of the gain adjustment unit is set to such a value that a level of the signal input into the A/D converter is in a suitable state.

A third aspect is the laser gas analyzer according to the first or second aspect, wherein the gain adjustment unit includes at least one window comparator.

Accordingly, the gain of the gain-variable amplifier can be adjusted so that the peak-to-peak value is in a suitable state as the level of the signal input into the A/D converter in each scan of the wavelength of laser light irradiated from a diode laser (that is, for each sampling).

A laser gas analyzer according to the present embodiment (present laser gas analyzer) will be described in detail below using the drawings. FIG. 1 is a block diagram showing the present laser gas analyzer. In FIG. 1, the same reference numerals are attached to members used in common with FIG. 2. In the present laser gas analyzer shown in FIG. 1, in contrast to the analyzer shown in FIG. 2, a P-P detector 37 and a gain adjustment unit 38 as members that adjust the gain of the gain-variable amplifier 32 are included. The P-P detector 37 detects a P-P value of output data from the A/D converter 33.

In the present laser gas analyzer shown in FIG. 1, the diode laser 11 is provided in the light source unit 10. The diode laser 11 irradiates an atmosphere of the gas to be measured 20 with measuring laser light. At this point, the wavelength of the laser light irradiated from the diode laser 11 is scanned in a narrow band containing an absorption wavelength to determine an area of an absorption spectrum of a component to be measured in the gas to be measured 20.

The measuring laser light having passed through the atmosphere of the gas to be measured 20 is received by the light receiving element 31 provided in the detection unit 30. The light receiving element 31 converts the received laser light into an electric signal.

An output signal from the light receiving element 31 is adjusted by the gain-variable amplifier 32 so that the signal has an amplitude level suitable as the level of a signal input into the A/D converter 33. Subsequently, the output signal is input into the A/D converter 33. The A/D converter 33 converts the signal into a digital signal.

Output data from the A/D converter 33 is added up by the integrating meter 34 before being stored in the memory 35. The additions and storages are repeated in synchronization with wavelength scans of the diode laser 11 a predetermined number of times (a few hundred to a few thousand times). Accordingly, noise contained in a measurement signal (output data) is removed. As a result, the output data is smoothed. Subsequently, the smoothed output data is input into the CPU 36.

The CPU 36 performs arithmetic processing such as the concentration analysis of the gas to be measured based on the measurement signal from which noise has been removed.

The P-P detector 37 detects the P-P value of output data of the A/D converter 33 in real time each time the wavelength of the diode laser 11 is scanned (each sampling). Then, the P-P detector 37 inputs a detection result into the gain adjustment unit 38. More specifically, the P-P detector 37 compares data values in real time in accordance with the timing of sampling by the A/D converter 33.

If an output signal of the P-P detector 37 deviates from a preset threshold, the gain adjustment unit 38 outputs, for the next scan, a control signal to adjust the gain of the gain-variable amplifier 32 to the amplifier 32 in a direction of bringing the output signal back to within the threshold. As the gain adjustment unit 38, for example, a member containing a window comparator is used.

If an abrupt environment change occurs such as extraneous noise arising suddenly in a period of a sequence of analysis processing, the P-P detector 37 accurately detects the P-P value of the A/D converter 33 in real time and outputs the detection result to the gain adjustment unit 38.

Then, the gain adjustment unit 38 determines whether the detection result of the P-P value input from the P-P detector 37 in sampling a period of the scan is an overflow state or an extremely low-level state when compared with the proper input level to the A/D converter 33 based on the preset threshold. For the next scan, the gain adjustment unit 38 outputs, to the amplifier 32, a control signal to adjust the gain of the gain-variable amplifier 32 in a direction of bringing the P-P value back to within the threshold.

Accordingly, even if an abrupt environment change occurs such as extraneous noise arising suddenly in a period of a sequence of analysis processing, the P-P value of output data of the A/D converter 33 is determined when one scan ends. The gain of the amplifier 32 can be changed so that the P-P value of the output data is at a proper input level to the A/D converter 33 in the next sampling.

By repeating such gain adjustments, the gain of the amplifier 32 can be adjusted properly for each scan of the wavelength of laser light. Thus, the overflow of output data of the A/D converter 33 and an extremely low level thereof can be avoided. Therefore, output of an erroneous analysis result can be prevented by analyzing output data. Consequently, highly accurate analysis results can typically be output. As a result, a laser gas analyzer suitable for direct measurement of process gases in various process industries can be realized.

The gain adjustment unit 38 may include a plurality of window comparators. In such a configuration, there is no need to adjust the gain of the amplifier 32 one step at a time. Thus, even when the level of the P-P value of output data of the A/D converter 33 changes significantly, the gain of the gain-variable amplifier 32 can be changed to an optimal value at a time.

The gain adjustment unit 38 may be any unit having substantially the same function as a window comparator and is not limited to the window comparator.

According to the present laser gas analyzer, as described above, suitable gain adjustments can be made in each scan. As a result, the present laser gas analyzer can output, with the application of the spectral area method, highly accurate analysis results over a long period, with stability, in real time, and at high speed. Therefore, the present laser gas analyzer is effective for direct measurement of various process gases.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A laser gas analyzer comprising:
   a light source unit including a diode laser that irradiates a gas to be measured with laser light while scanning a wavelength thereof;
   a detection unit including a light receiving element that detects the laser light having passed through the gas to be measured,
   a gain-variable amplifier into which an output signal of the light receiving element is input,
   an A/D converter into which the output signal of the amplifier is input, and
   an arithmetic processing unit that performs a concentration analysis of the gas to be measured based on output data of the A/D converter;
   a peak-to-peak detector that detects a peak-to-peak value of the output data of the A/D converter in each scan of the wavelength of the laser light irradiated from the diode laser; and
   a gain adjustment unit that, when the output signal of the peak-to-peak detector deviates from a preset threshold, adjusts the gain of the amplifier in a direction of bringing the output signal back to within the threshold.

2. The laser gas analyzer according to claim 1, wherein the threshold of the gain adjustment unit is set to such a value that a level of the signal input into the A/D converter is in a suitable state.

3. The laser gas analyzer according to claim 1, wherein the gain adjustment unit includes at least one window comparator.

4. The laser gas analyzer according to claim 2, wherein the gain adjustment unit includes at least one window comparator.

* * * * *